United States Patent
Andersson

(10) Patent No.: US 11,293,887 B2
(45) Date of Patent: Apr. 5, 2022

(54) APPARATUS FOR ANALYSIS OF METALS

(71) Applicant: NOVACAST SYSTEMS AB, Ronneby (SE)

(72) Inventor: Robert Andersson, Karlskrona (SE)

(73) Assignee: NOVACAST SYSTEMS AB, Ronneby (SE)

( * ) Notice: Subject to any disclaimer, the term of this patent is extended or adjusted under 35 U.S.C. 154(b) by 189 days.

(21) Appl. No.: 15/737,346

(22) PCT Filed: Jun. 16, 2016

(86) PCT No.: PCT/SE2016/050585
§ 371 (c)(1),
(2) Date: Dec. 18, 2017

(87) PCT Pub. No.: WO2016/204683
PCT Pub. Date: Dec. 22, 2016

(65) Prior Publication Data
US 2018/0164235 A1    Jun. 14, 2018

(30) Foreign Application Priority Data
Jun. 16, 2015  (GB) ..................................... 1510588

(51) Int. Cl.
*G01N 25/04* (2006.01)
*G01N 33/205* (2019.01)
(Continued)

(52) U.S. Cl.
CPC .............. *G01N 25/04* (2013.01); *G01N 1/10* (2013.01); *G01N 21/255* (2013.01); *G01N 33/205* (2019.01); *G01N 1/125* (2013.01)

(58) Field of Classification Search
CPC ...... G01N 1/125; G01N 25/04; G01N 33/205; G01N 33/025; G01N 1/10
(Continued)

(56) References Cited

U.S. PATENT DOCUMENTS 4,699,014 A    10/1987  Boron
4,731,732 A *  3/1988  Warchol ............. G01N 33/2025
                                                        702/24

(Continued)

FOREIGN PATENT DOCUMENTS

CN    104316377 A  *  1/2015
GB       1565215 A      4/1980
(Continued)

OTHER PUBLICATIONS

International Search Report, Application No. PCT/SE2016/050585, dated Sep. 21, 2016, 3 pages.

*Primary Examiner* — Gail Kaplan Verbitsky
(74) *Attorney, Agent, or Firm* — Ziegler IP Law Group, LLC

(57) ABSTRACT

An apparatus for analysis of metals is provided. The apparatus includes a molding cavity for receiving a sample of a molten metal, a gating system for allowing the molten metal to be poured, and a vent for allowing gases to escape from the apparatus when the molten metal is poured. The apparatus further includes at least one chill plate, adjacent to the molding cavity, for enabling faster cooling and solidification of the sample of the molten metal. The apparatus also includes a longitudinal slot, extending from the molding cavity, for allowing a sensor element to be introduced into the sample of the molten metal, the sensor element is a thermocouple wire that is used to monitor a cooling curve of the molten metal, while the molten metal solidifies.

15 Claims, 5 Drawing Sheets

(51) Int. Cl.
　　　*G01N 1/10*　　　(2006.01)
　　　*G01N 21/25*　　(2006.01)
　　　*G01N 1/12*　　　(2006.01)
(58) Field of Classification Search
　　　USPC .................................. 374/139, 43; 136/234
　　　See application file for complete search history.

(56) References Cited

U.S. PATENT DOCUMENTS

| | | | | |
|---|---|---|---|---|
| 4,737,038 | A * | 4/1988 | Dostoomian | G01J 5/0037 |
| | | | | 250/577 |
| 5,979,253 | A * | 11/1999 | Knevels | G01N 1/125 |
| | | | | 73/864.58 |
| 6,200,520 | B1 * | 3/2001 | Morinaka | G01N 33/205 |
| | | | | 266/79 |
| 6,257,004 | B1 * | 7/2001 | Gendron | B22D 11/225 |
| | | | | 164/455 |
| 9,645,055 | B2 * | 5/2017 | Cappa | G01N 1/125 |
| 2003/0086473 | A1 * | 5/2003 | Popelar | G01N 33/205 |
| | | | | 374/139 |
| 2010/0142585 | A1 * | 6/2010 | Popelar | G01N 1/125 |
| | | | | 374/139 |
| 2013/0223477 | A1 * | 8/2013 | Hiraoka | G01N 1/125 |
| | | | | 374/139 |
| 2018/0164193 | A1 * | 6/2018 | Beyens | G01N 33/205 |

FOREIGN PATENT DOCUMENTS

JP　　　　2015178120 A　*　10/2015
KR　　　20090103244 A　　　10/2009

* cited by examiner

SECTION A-A

SECTION B-B

APPARATUS FOR ANALYSIS OF METALS

TECHNICAL FIELD

The present disclosure relates generally to metal and material analysis; and more specifically, to apparatuses and methods for analysis of metals.

BACKGROUND

There are various evaluation methods for determining a chemical composition of a specimen of cast iron. Most commonly, these evaluation methods employ:
(i) a spectrometer analysis, for example using an optical spectrometer,
(ii) a combustion analysis, for example using a Laboratory Equipment Corporation (LECO) machine, or
(iii) a thermal analysis.

In the spectrometer analysis, an optical spectrometer (see reference [1]) is used to measure properties of light over a specific portion of the electromagnetic spectrum to determine a composition of a specimen. Typically, the specimen is cast from molten metal into a cylindrical shape, for example, having a diameter ranging between 30 mm and 40 mm and a thickness ranging between 3 mm to 5 mm.

In order to make an accurate analysis of the specimen, it is important that the specimen has a homogenous microstructure, namely a uniform composition and density, and that each component in the microstructure is as small as possible. An example of a cast iron specimen having a homogeneous microstructure is white iron in which carbon remains interspersed in the metal in a form of a carbide, instead of precipitating out in a form of graphite. Materials like tellurium have been used to prevent formation of graphite in the metal. Such materials are typically coated on inner surfaces of a mold being used for molding the specimen or placed in the mold in a form of an insert.

During molding, the molten metal undergoes a solidification process that is according to a metastable phase diagram of white iron, namely iron of carbide type. For this purpose, the specimen is cast in a metal mold, which results in a fast cooling and solidification process.

However, there are some challenges when casting a specimen in a metal mold. The specimen may have inner defects arising from formation of slags and oxides and/or may have a rough outer surface quality. Typically, the specimen is grinded or machined before any analysis is performed. Moreover, in several foundries, metal molds are used repeatedly for casting a large number of specimens during a shift. As a result, mold temperatures increase during the shift, and adversely affect a cooling effect of the metal molds. This leads to a formation of an uneven microstructure in the specimens, which, in turn, has a negative effect on the accurateness of the spectrometer analysis.

Furthermore, in the combustion analysis, a method that is based on combustion technology, for example, such as a LECO type of method, is used. Such a method requires that small pieces of metal be machined out from a given specimen. In some cases, the metal pieces are machined out from the same specimen that has been used for the thermal analysis. The metal pieces may, for example, be obtained using a turning or boring operation, which typically has high demands for hygiene. The metal pieces are then placed in a small ceramic crucible, and reheated and melted under a strictly controlled atmosphere. The specimen is then combusted in the presence of pure oxygen. During this process, carbon and sulphur are oxidized to form carbon dioxide ($CO_2$) and sulphur dioxide ($SO_2$), respectively.

A well-serviced combustion analysis successfully detects low levels of carbon, sulphur, nitrogen, oxygen and hydrogen, for example ranging between 0.0002 and 0.05 percentage, depending upon a type of specimen. The combustion analysis yields an exact result, but requires a high hygiene, a good service level, a lab atmosphere, and a quite expensive equipment.

Furthermore, the thermal analysis is based on a fact that, when solidifying according to the metastable phase diagram, solidification characteristics of a cast iron specimen have a clear relation to the composition of the specimen, namely to Carbon Equivalent Liquidus (CEL) content and Carbon content.

In the thermal analysis, a ceramic cup with typical dimensions of 35 mm×35 mm×40 mm (b×w×h) is filled with molten cast iron. On the bottom or the sides of the cup, a tellurium paste is coated or glued to the cup. Tellurium has a high affinity to sulphur. When sulphur is tied up with tellurium atoms, the cast iron solidifies according to the metastable phase diagram. The weight of the metal ranges between 190 g and 250 g, depending on a fill status of the cup.

Typically, a thermocouple that extends into the cup or is positioned centrally in the cup is used to monitor a cooling curve of the molten cast iron. A drop in temperature along the cooling curve during the solidification is logged by a measuring device. The measuring is finished after certain time, for example, after 70-180 seconds. The composition of the metal is then determined based on a form of the cooling curve.

Thermal analysis is a well-established technology, and in most cases, is used in parallel with the spectrometer analysis and/or the combustion analysis. Thermal analysis gives accurate and fast results. Moreover, practical implementation of thermal analysis is easy and robust. However, tellurium used in this process is dangerous for the environment and health of operators. The specimen cannot be re-cycled easily because of the presence of tellurium, and has to be sent for external recycling.

SUMMARY

The present disclosure seeks to provide an improved apparatus and a method for analysis of metals.

The present disclosure also seeks to provide an improved apparatus and a method for analysis of cast iron without use of tellurium.

A further aim of the present disclosure is to at least partially overcome at least some of the problems of the prior art, as discussed above.

In one aspect, embodiments of the present disclosure provide an apparatus for analysis of metals, characterized in that the apparatus comprises:
a mold cavity for receiving a sample of a molten metal;
a gating system, extending from the mold cavity, for allowing the molten metal to be poured;
a vent, extending from the mold cavity, for allowing gases to escape from the apparatus when the molten metal is poured;
at least one chill plate adjacent to the mold cavity for enabling cooling and solidification of the sample of the molten metal; and
a longitudinal slot, extending from the mold cavity, for allowing a sensor element to be introduced into the mold cavity, the sensor element is a thermocouple wire that is used to monitor a cooling curve of the molten metal, while the molten metal solidifies.

In another aspect, embodiments of the present disclosure provide a method for analysis of metals, characterized in that the method comprises:

pouring a sample of a molten metal into a mold cavity through a gating system extending from the mold cavity;

cooling and solidifying the sample of the molten metal using at least one chill plate adjacent to the mold cavity;

measuring temperature of the cooling and solidifying sample of the molten metal using a sensor element, to be introduced into the molten metal through a longitudinal slot extending from the mold cavity, wherein the sensor element is a thermocouple wire; and generating a cooling curve of the molten metal using the detected temperature while the molten metal solidifies.

The apparatus is designed in a manner that a test specimen of a smaller size is produced in a faster cooling and solidification process, as compared to conventional apparatuses. As a result of the faster cooling and solidification process, materials like tellurium are not required to be used.

Embodiments of the present disclosure substantially eliminate or at least partially address the aforementioned problems in the prior art, and enable a fast analysis of cast iron and ductile iron, without use of tellurium.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1C:
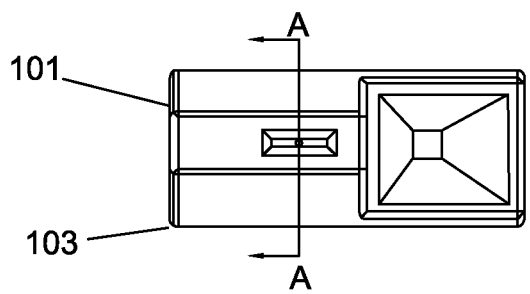
FIGS. 1A and 1C are a side view and a top view respectively an apparatus for analysis of metals, in accordance with an embodiment of the present disclosure.

In the accompanying drawings, a non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, embodiments of the present disclosure provide an apparatus for analysis of metals, characterized in that the apparatus comprises:

a mold cavity for receiving a sample of a molten metal;

a gating system, extending from the mold cavity, for allowing the molten metal to be poured;

a vent, extending from the mold cavity, for allowing gases to escape from the apparatus when the molten metal is poured;

at least one chill plate adjacent to the mold cavity for enabling cooling and solidification of the sample of the molten metal; and a longitudinal slot, extending from the mold cavity, for allowing a sensor element to be introduced into the molten metal, the sensor element is a thermocouple wire that is used to monitor a cooling curve of the molten metal, while the molten metal solidifies.

In another aspect, embodiments of the present disclosure provide a method for analysis of metals, characterized in that the method comprises:

pouring a sample of a molten metal into a mold cavity through a gating system extending from the mold cavity;

cooling and solidifying the sample of the molten metal using at least one chill plate adjacent to the mold cavity;

measuring temperature of the cooling and solidifying sample of the molten metal using a sensor element, to be introduced into the molten metal through a longitudinal slot extending from the mold cavity, wherein the sensor element is a thermocouple wire; and generating a cooling curve of the molten metal using the detected temperature while the molten metal solidifies.

The apparatus and method are susceptible to being used for thermal analysis and spectrometer analysis of metal, such as grey iron, ductile and compacted graphite iron.

The at least one chill plate enables the apparatus to achieve a high cooling and solidification rate, namely a faster process of cooling and solidification of the molten metal (hereinafter referred to as "faster cooling and solidification process"). It will be appreciated that a high cooling and solidification rate is necessary to achieve a TE White state in the metal, without use of materials like tellurium. The term "TE White" used herein refers to a temperature for white solidification of the metal, namely a lower temperature in an eutectic temperature interval of the metastable phase diagram of white iron. In the eutectic temperature interval, the metal is in a form of a mix between melt and solid phases.

According to an embodiment, the at least one chill plate is implemented in a form of an internal chill.

The at least one chill plate can be formed from various metals or alloys, for example, such as ductile iron, copper, or steel. According to an embodiment, the at least one chill plate is formed from low-grade steel.

The gating system and the vent extend from the mold cavity towards outside ending at a bottom and a top, respectively, of the mold cavity of the apparatus, preferably in slightly different directions with respect to each other. For example, the gating system and the vent may be located at an angle of from 90-170° with respect to each other. Further, the gating system is wide enough to permit a high pouring speed of the molten metal into the mold cavity. Moreover, the configuration of the gating system at the bottom allows the molten metal to be filled in the mold cavity in a bottom up direction.

Thus, the apparatus is designed in a manner that a test specimen of a smaller size is produced in a faster cooling and solidification process, as compared to conventional apparatuses. As a result of the faster cooling and solidification process, materials like tellurium are not required to be used. This facilitates a decrease in an environmental load with regard to use of tellurium. This also enables the test specimen to be re-melted in a foundry and re-cycled easily.

Moreover, the test specimen so formed is clean with a high surface quality, and has minimal risks for occurrences of casting defects, such as cold laps and cold shuts.

According to an embodiment, the apparatus is suitable for casting a test specimen of a thickness ranging from 3 mm to 10 mm, preferably 3.5-4.5 mm. In an embodiment, the sample of the molten metal (specimen) may be configured to attain a coin shape, based on the shape of the mold cavity.

Moreover, the apparatus is suitable for determining a chemical composition of various metals, for example of cast iron or ductile iron or grey iron or ductile compacted graphite iron. The apparatus is particularly suitable for a fast analysis of cast iron and ductile iron without the use of tellurium. It will be appreciated here that the apparatus is suitable for analysis of ductile iron, as it enables a faster cooling and solidification process to be achieved without the use of tellurium. Conventional apparatuses that use tellurium are unsuitable for analysis of ductile iron, as tellurium reacts with ductile iron and is unavailable for tying up sulphur; as a result, ductile iron does not solidify properly, namely according to a metastable phase diagram of white iron.

Furthermore, according to an embodiment, the apparatus also comprises a longitudinal slot, extending from the mold cavity, for allowing a sensor element to be introduced into the sample of the molten metal. Specifically, the longitudinal slot is configured at a bottom of the mold cavity. This longitudinal slot also extends from the mold cavity towards the outside of the apparatus. In one embodiment, the longitudinal slot is diametrically opposed to the gating system, i.e. they are located at 180° one from another.

In an embodiment, the sensor element is preheated by the molten metal before the mold cavity is filled with the molten metal. In other words, the sensor element is preheated to reach a temperature that of the molten metal prior to be introduced into the mold cavity. This enables or ensures a reliable analysis, i.e. thermal analysis, to be performed with the help of temperature to be measured from cooling and solidifying sample of the molten metal by the sensor element. Specifically, the sensor element is introduced in the bottom of the mold cavity and is preheated by the molten metal before the mold cavity is filled with the molten metal. For example, the sensor element is inserted in the longitudinal slot such that sensor element protrudes in the mold cavity before the start of the pouring the molten metal into the mold cavity. Therefore, when the molten metal enters the cavity and the sensor element is preheated, the sensor element is ready to start the thermal analysis when the mold cavity is completely filled. Further, a part of the sensor protruding in the mold cavity is broken and stays in the solidified sample when released from the apparatus.

In one embodiment, a steel sleeve may be mounted at the bottom of the mold cavity to receive the sensor therein. This may allow reusability of the sensor element.

According to an embodiment, the sensor element is a thermocouple wire that is used to monitor a cooling curve of the molten metal, while the molten metal solidifies. This enables a thermal analysis of the metal to be performed. When the metal solidifies, the test specimen is formed in a shape of the mold cavity. The test specimen is then used for a spectrometer analysis.

In operation, the mold cavity is filled with molten metal, thereafter the temperature is measured with a high frequency (minimum 50 times per sec) temperature measuring unit, such as a temperature sensor unit. In an embodiment, the temperature measuring unit may include functional electronic components, which includes but not limited to at least one temperature sensor, a processor, a memory and so forth. In an example, the temperature sensor unit is operable to define first and second derivatives for each measured temperature value. Thereafter, based on the first and second derivatives a cooling graph of the sample of the molten metal may be determined.

In one embodiment, the temperature sensor unit is further operable to determine liquidus temperature, eutectic temperature and solidus temperature using the cooling curve, the first and second derivatives. For example, an algorithm (stored in the memory) may be executable on the processor using the cooling curve, the first and second derivatives to determine the liquidus temperature, the eutectic temperature and the solidus temperature.

The chill plate in the mold cavity determines a molten metal solidification time which is about 5-17 seconds (s), preferably 13-17 s, and most preferablyby 15 s by means of a predetermined relationship between a thickness of the chill plate and a depth of the mold cavity. Specifically, the thickness of the chill plate and the depth of the mold cavity are adjusted in a manner such that a faster solidification time (or rate) for the molten metal may be achieved. In an embodiment, the thickness of the chill plate may be in a range of 1.5 mm to 2.5 mm, preferably 2.5 mm. Further, the mold cavity may include a diameter of about 47 mm and a depth in a range of 5.5 mm to 6.5 mm. This predetermined structural relationship may suitably yield a solidified sample of a molten metal having a thickness of about 3.5-4.5 mm. The predetermined relationship between the thickness of the chill plate and the depth of the mold cavity also enables in formation of a layer of white iron on top of the cooled and solidified sample of the molten metal. The sample of the molten metal, having layer of white iron on top, is suitable for a spectrometer analysis. In an example, the faster solidification time (or rate) yields a 1-2 mm thick layer of white iron on top the sample of the molten metal.

Thus, the apparatus enables a same test specimen of metal to be used for the thermal analysis and the spectrometer analysis. This is important for traceability purposes. The thermal analysis facilitates a high precision determination of Carbon Equivalent Liquidus (CEL) content, carbon content and silica content in the test specimen, while the spectrometer analysis facilitates a high precision determination of heavy elements, namely heavy metals, present in the test specimen.

Another advantage of using the same test specimen for both the analyses is that the analysis of the metal is fast.

According to an embodiment, a main body of the apparatus is made of a mold material that has a low impact both on the environment and operators handling the apparatus. In an embodiment, the main body of the apparatus is made of sand (or sand composition), which may be an environment-friendly core sand. For example, the environment-friendly core sand may include green sand. It is to be noted here that other suitable "green" core materials could be used instead of green sand.

The term "green sand" generally refers to wet sand that is used to make a mold's shape. A green sand is not a particular type of sand on its own, but is rather a mixture (see reference [2]). As an example, green sand could comprise 75 to 85% of silica sand ($SiO_2$), 5 to 11% of abentonite (namely, clay), 2 to 4% of water, 3 to 5% of an inert sludge, and 0 to 1% of an anthracite.

As the apparatus is made from green sand or other suitable "green" core materials, the apparatus is expendable. The green sand could be recycled in a normal recycling system.

According to an embodiment, the apparatus is made from two mold halves, in a manner that when the two mold halves are separated, the apparatus is split vertically. Further, when halves put together a slot is provided in a periphery of the mold cavity, the slot extends along the periphery of the mold cavity from the gating system into the mold cavity up to the vent. The slot is typically provided opposite the chill plate. A length of the slot may vary based on an overall size of the apparatus. Further, the slot ensures a short fill time for the cavity. Moreover, the short fill time without turbulence in the flow of molten material avoids defects in the sample caused by gas or slag occlusions. Also, the short fill time will also ensure a high surface smoothness. In operation, the mold halves are aligned and clamped together, for example, with a clamp of steel. According to an embodiment, neither ceramic glue nor ceramic paste is used in the apparatus.

According to an embodiment, the thermocouple wire is made of Chromel-Alumel type.

According to an embodiment, at least a portion of the thermocouple wire is covered with a protective ceramic material. An example of the ceramic material is an $Al_2O_3$ material.

Moreover, optionally, the results of the analyses are saved into a central server. Optionally the results of the analyses are displayed in parallel to a production staff.

DETAILED DESCRIPTION OF DRAWINGS

Figure 1D:
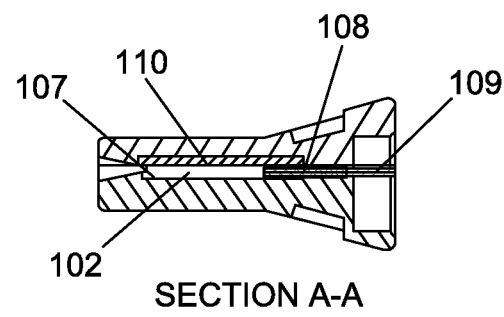
FIGS. 1B and 1D are sections B-B and A-A in FIGS. 1A and 1C respectively.
Figure 1A:
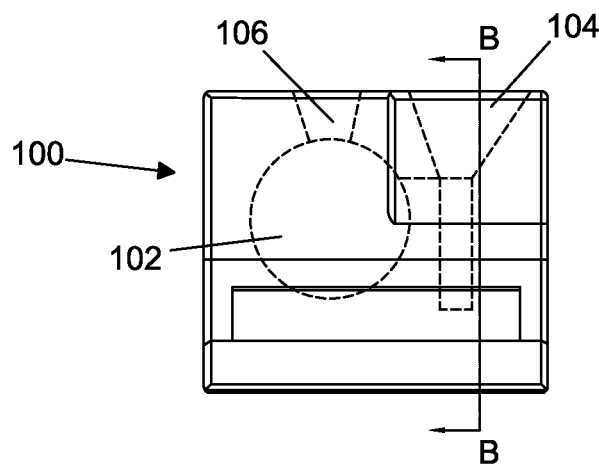
Figure 1B:
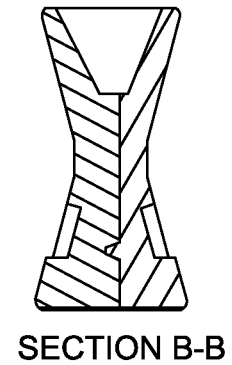

Referring now to the drawings, particularly by their reference numbers, FIGS. 1A and 1C are schematic illustrations of an apparatus 100 for analysis of metals, in accordance with an embodiment of the present disclosure.

The apparatus 100 includes a mold cavity 102 for receiving a sample of a molten metal, a gating system 104 for allowing the molten metal to be poured, a vent 106 for allowing gases to escape, and a longitudinal slot 108 for allowing a sensor element to be introduced into the sample of the molten metal.

FIG. 1D is a section through the mold cavity and shows specifically a chill plate 110 placed in the mold half 101 and a recess 107 in the other mold half 103. The recess provides a peripheral slot together with the opposite mold half and contributes to a short fill time of the cavity.

Figure 2A:
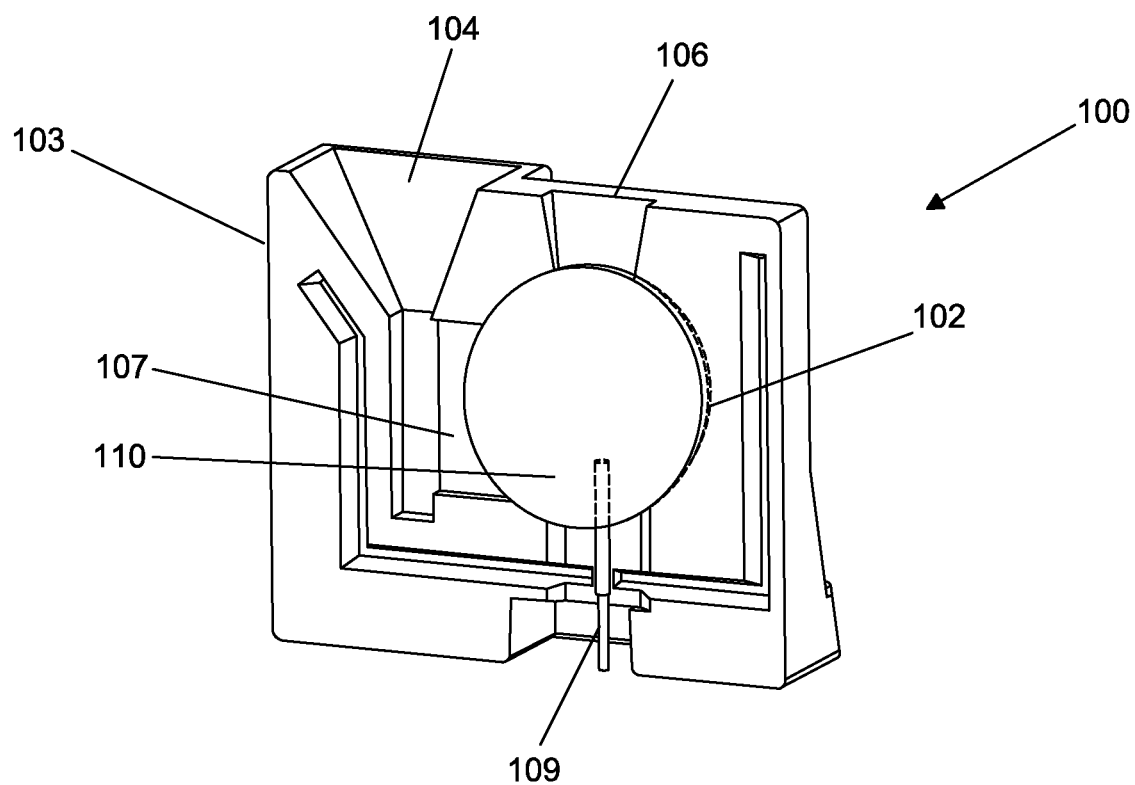
FIGS. 2A and 2B are perspective views of a respective mold half of the embodiment in FIG. 1 A-D

In FIG. 2A, there is shown a perspective view of a mold half 103 of the apparatus 100. The recess 107 extends along the periphery of the mold half 103 from a point near the bottom of the cavity to a point near the vent 106. A sensor element 109 is inserted in the bottom of the cavity 102. When molten metal is inserted in the cavity through the slot between the mold halves the sensor element is preheated.

Figure 3:
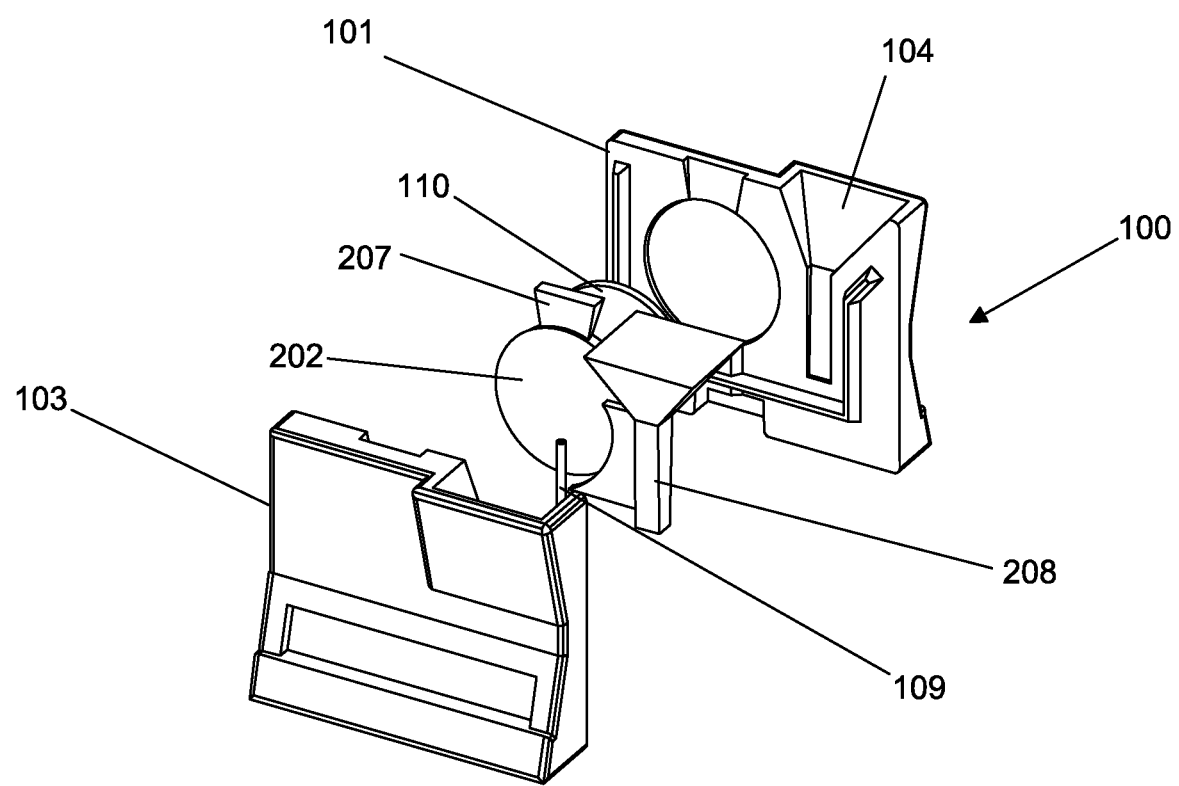
FIG. 3 is an exploded view of an apparatus in accordance the embodiment in FIGS. 1 and 2 in which a sample has been molded.

In FIG. 3, there is shown an exploded view of the apparatus 100, in which a residue 202 is a result of a solidification of molten metal filled in the apparatus according the showed embodiment of the invention. Unwanted portions of excess metal 207 and 208 of the residue 202 are cut to obtain a test specimen of a coin shape, for example, for spectrometer analysis.

Figure 2B:
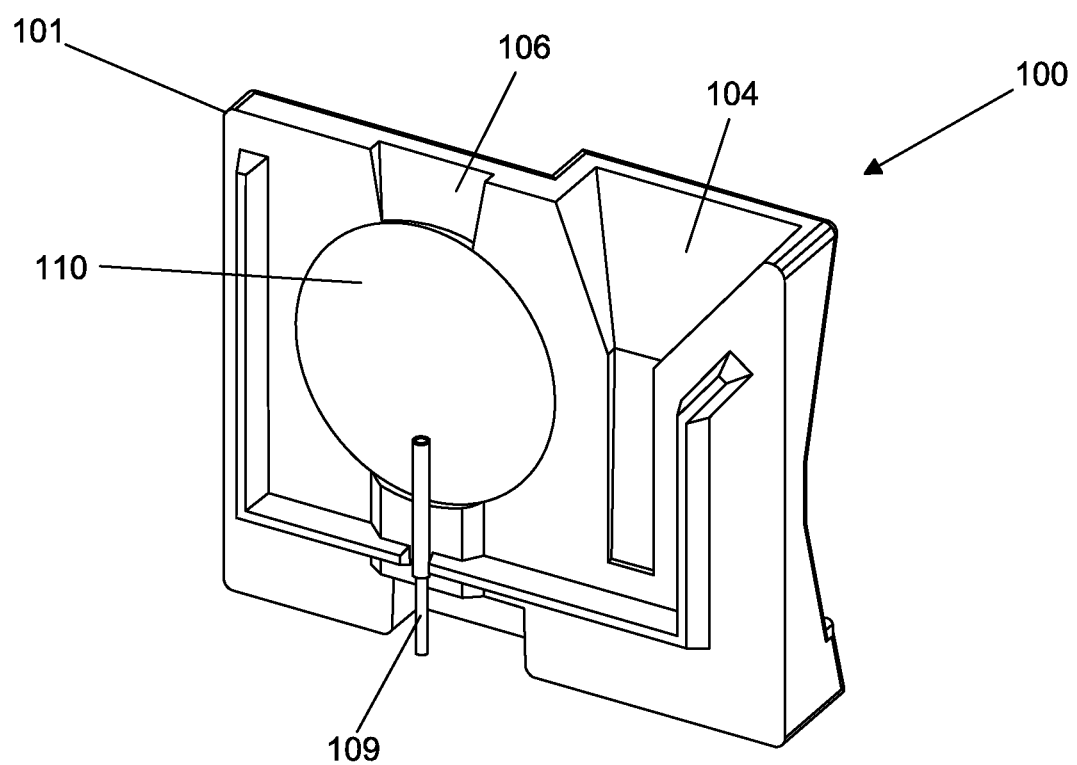

FIGS. 1 to 3 are merely examples. A person skilled in the art will recognize many variations, alternatives, and modifications of embodiments of the present disclosure.

Figure 4:
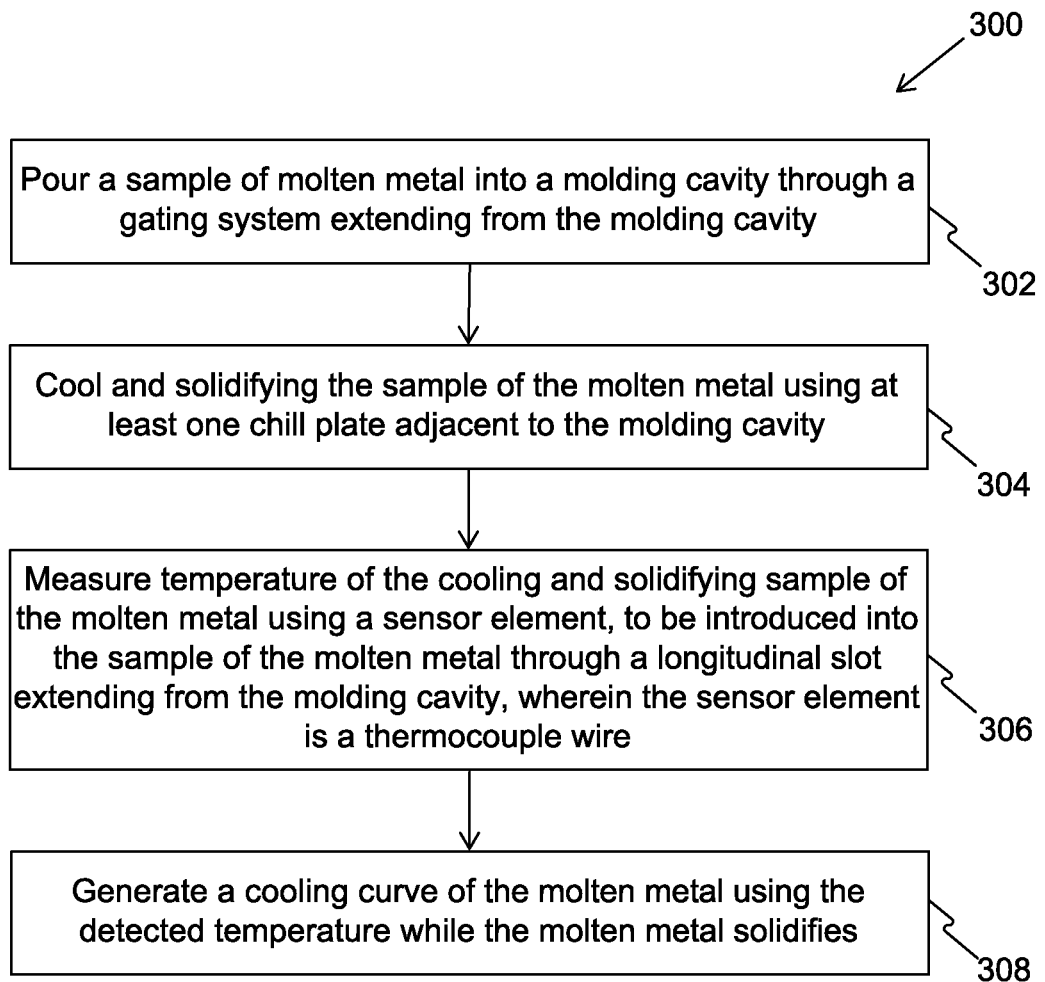
FIG. 4 is an illustration of steps of a method for analysis of metals, in accordance with an embodiment of the present disclosure.

FIG. 4 is an illustration of steps of a method 300 for analysis of metals, in accordance with an embodiment of the present disclosure.

Specifically, those skilled in the art would recognize that the method 300 illustrates steps involved in the functioning of an apparatus, such as apparatuses 100 and 200, explained in conjunction with the FIGS. 1 to 3.

At step 302, a sample of a molten metal is poured into a mold cavity through a gating system extending from the mold cavity.

At step 304, the sample of the molten metal is cooled and solidifyed using at least one chill plate adjacent to the mold cavity.

At step 306, temperature of the cooling and solidifying sample of the molten metal is measured using a sensor element. The sensor element is operable to be introduced into the sample of the molten metal through a longitudinal slot extending from the mold cavity. The sensor element is a thermocouple wire.

At step 308, a cooling curve of the molten metal is generated using the detected temperature as the molten metal solidifies.

The steps 302 to 308 are only illustrative and other alternatives can also be provided where one or more steps are added, one or more steps are removed, or one or more steps are provided in a different sequence without departing from the scope of the claims herein. For example, the method 300 may further include venting gases from the mold cavity by a vent extending from the mold cavity.

Further, the method 300 may include preheating the sensor element prior to introducing into the sample of the molten metal. Moreover, in the method 300, the measuring of the temperature of the cooling and solidifying sample may include defining first and second derivatives for each measured temperature value, and thereafter determining liquidus temperature, eutectic temperature and solidus temperature using the cooling curve, the first and second derivatives. The method 300 may also include defining carbon content, silica content and carbon equivalent liquidus content by using the cooling curve. The method 300 may further include performing spectrometer analysis on the cooled and solidified sample of the molten metal. The method 300 may also include grinding the cooled and solidified sample of the molten metal prior to the spectrometer analysis.

Embodiments of the present disclosure are susceptible to being used for various purposes, including, though not limited to, enabling a fast analysis of cast iron and ductile iron, without use of tellurium. Further, embodiments of the present disclosure are susceptible to being used for thermal analysis and spectrometer analysis of such metal.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. An apparatus for analysis of metals, wherein the apparatus comprises:
   a molding cavity for receiving a sample of a molten metal;
   a gating system for allowing the molten metal to be poured;
   a recess slot extending between the gating system and the molding cavity for allowing the molten metal to flow from the gating system to the molding cavity;
   a vent, extending from the molding cavity, for allowing gases to escape from the apparatus when the molten metal is poured;
   at least one chill plate, adjacent to the molding cavity, for enabling cooling and solidification of the sample of the molten metal; and
   a longitudinal slot, extending from the molding cavity, for allowing a sensor element to be introduced into the molding cavity, the sensor element is a thermocouple wire that is used to monitor a cooling curve of the molten metal, while the molten metal solidifies,
   wherein the apparatus comprises mold halves that, when put together, provide the recess slot at a portion of a periphery of the molding cavity and the recess slot extends along the periphery of the molding cavity from a height of a bottom of the gating system,
   wherein the sensor element is introduced in the bottom of the molding cavity and is preheated by the molten metal before the molding cavity is filled with the molten metal, and
   wherein the gating system allows the molten metal to be filled in the molding cavity in a bottom up direction.

2. An apparatus as claimed in claim 1, wherein the at least one chill plate is implemented in a form of an internal chill.

3. An apparatus as claimed in claim 1, wherein the gating system ends at a bottom of the molding cavity.

4. An apparatus as claimed in claim 1, wherein the recess slot extends along the periphery of the molding cavity from the gating system into the molding cavity up to the vent.

5. An apparatus as claimed in claim 1, wherein a thickness of the chill plate is in a range of 1.5 mm to 2.5 mm, preferably 2.5 mm and a depth of the molding cavity is in a range of 5.5 mm to 6.5 mm to enable fast solidification of the molten metal and formation of a layer of white iron on the sample of the molten metal.

6. An apparatus as claimed in claim 1, wherein the apparatus is suitable for casting a test specimen of a thickness ranging from 3 mm to 10 mm.

7. An apparatus as claimed in claim 1, wherein the apparatus is suitable for analyzing cast iron.

8. An apparatus as claimed in claim 1, wherein the apparatus is suitable for analyzing ductile iron.

9. An apparatus as claimed in claim 1, wherein the apparatus enables a same test specimen of metal to be used for thermal analysis and spectrometer analysis.

10. An apparatus as claimed in claim 1, wherein a main body of the apparatus is made of sand.

11. An method for analysis of metals, wherein the method comprises:
    pouring a sample of a molten metal through a gating system;
    allowing the molten metal to flow from the gating system through a recess slot into a molding cavity, wherein the recess slot extends between the gating system and the molding cavity;
    cooling and solidifying the sample of the molten metal using at least one chill plate adjacent to the molding cavity;
    measuring temperature of the cooling and solidifying sample of the molten metal using a sensor element, to be introduced into the molding cavity through a longitudinal slot extending from the molding cavity, wherein the sensor element is a thermocouple wire; and
    generating a cooling curve of the molten metal using the detected temperature while the molten metal solidifies,
    wherein the recess slot is provided at a portion of a periphery of the molding cavity and the recess slot extends along the periphery of the molding cavity from a height of a bottom of the gating system,
    wherein the sensor element is preheated prior to introducing into the sample of the molten metal,
    wherein the gating system allows the molten metal to be filled in the molding cavity in a bottom up direction;
    and wherein the measuring of the temperature of the cooling and solidifying sample comprise:
       defining first and second derivatives with time for each measured temperature value, and
       determining liquidus temperature, eutectic temperature and solidus temperature using the cooling curve, the first and second derivatives with time for each measured temperature value.

12. The method as claimed in claim 11, further comprising venting gases from the molding cavity by a vent extending from the molding cavity.

13. The method as claimed in claim 11, further comprising defining carbon content, silica content and carbon equivalent liquidus content by using the cooling curve.

14. The method as claimed in claim 11, wherein further comprises performing spectrometer analysis on the cooled and solidified sample of the molten metal.

15. The method as claimed in claim 14, wherein further comprises grinding the cooled and solidified sample of the molten metal prior to the spectrometer analysis.

* * * * *